(12) United States Patent
Nishino et al.

(10) Patent No.: US 8,318,932 B2
(45) Date of Patent: Nov. 27, 2012

(54) PROCESS FOR PRODUCING 4-AMINOQUINAZOLINE COMPOUND

(75) Inventors: Shigeyoshi Nishino, Yamaguchi (JP); Kenji Hirotsu, Yamaguchi (JP); Hidetaka Shima, Yamaguchi (JP); Takashi Harada, Yamaguchi (JP); Hiroyuki Oda, Yamaguchi (JP)

(73) Assignee: Ube Industries, Ltd., Ube-shi, Yamaguchi (JP)

( * ) Notice: Subject to any disclaimer, the term of this patent is extended or adjusted under 35 U.S.C. 154(b) by 698 days.

(21) Appl. No.: 12/400,895

(22) Filed: Mar. 10, 2009

(65) Prior Publication Data

US 2009/0171083 A1 Jul. 2, 2009

Related U.S. Application Data

(63) Continuation of application No. 10/503,664, filed as application No. PCT/JP03/01254 on Feb. 6, 2003, now abandoned.

(30) Foreign Application Priority Data

Feb. 6, 2002 (JP) .................................... 2002-29745
Aug. 27, 2002 (JP) .................................. 2002-246656
Sep. 19, 2002 (JP) .................................. 2002-272892
Sep. 19, 2002 (JP) .................................. 2002-272893

(51) Int. Cl.
*C07D 239/72* (2006.01)
(52) U.S. Cl. ........................................ 544/293; 544/287
(58) Field of Classification Search .................. 544/287, 544/293
See application file for complete search history.

(56) References Cited

U.S. PATENT DOCUMENTS

| 5,256,781 A | 10/1993 | Primeau et al. |
| 5,661,147 A | 8/1997 | Machii et al. |
| 5,747,498 A * | 5/1998 | Schnur et al. ............ 514/266.4 |
| 5,747,798 A | 5/1998 | Smith |
| 2008/0171083 A1 * | 7/2008 | Staniforth et al. ............ 424/456 |

FOREIGN PATENT DOCUMENTS

| JP | 5-208911 | 8/1993 |
| WO | 96-33980 | 10/1996 |
| WO | WO 9732856 A1 * | 9/1997 |
| WO | WO 9935146 A1 * | 7/1999 |
| WO | 00-47212 | 8/2000 |
| WO | WO 0055141 A1 * | 9/2000 |

OTHER PUBLICATIONS

A.J. Bridges et al., Journal of Medicinal Chemistry, 39, 267-276 (1996).*
S. Giorgi-Renault et al., Chemical and Pharmaceutical Bulletin, 36(10), 3933-3947 (1988).*
N.G. Anderson, Practical Process & Research Development 81-111, 114-143 (2000).*

* cited by examiner

*Primary Examiner* — James O Wilson
*Assistant Examiner* — Alexander R Pagano
(74) *Attorney, Agent, or Firm* — Nixon Peabody LLP; Jeffrey L. Costellia

(57) ABSTRACT

A 4-aminoquinazoline derivative can be obtained by the steps of reacting quinazolin-4-one or its derivative with a chlorinating agent in a first organic solvent in the presence of an organic base, and subsequently reacting the reaction product with an amine compound represented by the formula $R^5$—NH—$R^6$ (each of $R^5$ and $R^6$ represents hydrogen or an optionally substituted hydrocarbyl group) in the presence of a second organic solvent.

11 Claims, No Drawings

PROCESS FOR PRODUCING 4-AMINOQUINAZOLINE COMPOUND

FIELD OF THE INVENTION

The present invention relates to a process for preparing a 4-aminoquinazoline compound from a quinazolin-4-one compound. The 4-aminoquinazoline compound is useful as an intermediate or a starting compound for preparing a pharmaceutically active compound or an agricultural chemical.

The invention specifically relates to a process for preparing 6-halogeno-4-arylaminoquinazoline from 6-halogeno-quinazolin-4-one.

The invention further relates to a process for preparing 6-halogeno-4-chloroquinazoline from 6-halogenoquinazolin-4-one. The 6-halogeno-4-chloroquinazoline is employable as a starting compound for preparing the 6-halogeno-4-arylaminoquinazoline.

BACKGROUND OF THE INVENTION

JP-A-10-152477 describes a process for preparing a 4-arylaminoquinazoline compound from a quinazolin-4-one, which comprises the steps of chlorinating 4-iodoquinazolin-4-one using an excessive amount of oxalyl chloride to produce 6-iodo-4-chloroquinazoline (intermediate compound), concentrating the reaction product under reducing pressure to isolate the resulting product; reacting the 6-iodo-4-chloroquinazoline with 5-aminoindole to give 6-iodo-4 (5-indolylamino)quinazoline. Unfortunately, the yield is not high. Further, it should be noted that the intermediate compound, i.e., 4-chloroquinazoline compound, shows no satisfactory stability in the presence of water and no satisfactory resistance to heat. Accordingly, the compound should be handled carefully.

WO 96/09294 describes a process for preparing 6-halogeno-4-chloroquinazoline from 6-halogenoquinazolin-4-one which comprises reacting the 6-halogenoquinazolin-4-one with an excessive amount of phosphorus oxychloride. This process, however, has problems in that a large amount of smelly phosphorus oxychloride should be used, yield of the reaction product (i.e., 6-halogeno-4-chloroquinazoline) is low, and a large amount of an organic solvent is necessarily employed for recovering the reaction product from an excessive amount of phosphorus oxychloride. Thus, complicated post-treating procedures are required.

DISCLOSURE OF THE INVENTION

The present invention has an object to provide a simple process for preparing a 4-aminoquinazoline compound from a quinazolin-4-one compound.

The invention specifically has an object to provide a process for preparing 6-halogeno-4-arylaminoquinazoline from 6-halogenoquinazolin-4-one.

The invention further relates has an object to provide a process for preparing 6-halogeno-4-chloroquinazoline from 6-halogenoquinazolin-4-one. The 6-halogeno-4-chloroquinazoline is employable as a starting compound for preparing the 6-halogeno-4-arylaminoquinazoline.

The present invention resides in a process for preparing a 4-aminoquinazoline compound having the formula (3):

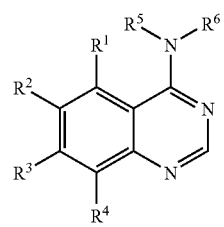

(3)

in which each of $R^1$, $R^2$, $R^3$ and $R^4$ independently represents a group not participating the below-mentioned reaction, or $R^1$, $R^2$, $R^3$ and $R^4$ are combined to form a ring, and each of $R^5$ and $R^6$ independently represents a hydrogen atom or a hydrocarbyl group which can have a substituent, which comprises:

a first step of reacting a quinazolin-4-one compound having the formula (1):

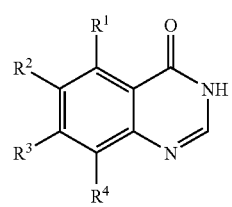

(1)

in which $R^1$, $R^2$, $R^3$ and $R^4$ have the same meaning as above, with a chlorinating agent in a first organic solvent in the presence of an organic base, and a second step for reacting a reaction product of the first step with an amine compound having the formula (2):

$R^5$—NH—$R^6$ (2)

in which $R^5$ and $R^6$ have the same meaning as above, in the presence of a second organic solvent.

The invention further resides in the process wherein the quinazolin-4-one compound of formula (1) is 6-halogeno-quinazolin-4-one of the following formula (4), the amine compound of formula (2) is arylamine of the following formula (5), and the 4-arylaminoquinazoline compound of formula (3) is 6-halogeno-4-arylaminoquinazoline of the following formula (6):

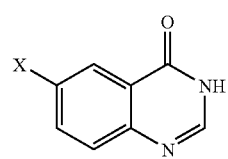

(4)

ArNH$_2$ (5)

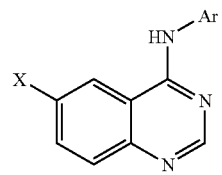

(6)

in which X is a halogen atom, and Ar is an aryl group which can have a substituent.

The invention furthermore resides in a process for preparing 6-halogeno-4-chloroquinazoline having the formula (7)

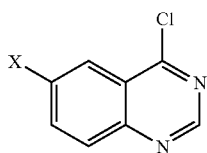

(7)

in which X is a halogen atom,
which comprises reacting 6-halogenoquinazolin-4-one having the formula (4):

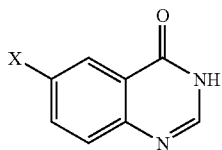

(4)

in which X has the same meaning as above,
with a chlorinating agent in an organic solvent in the presence of an organic base.

DETAILED DESCRIPTION OF THE INVENTION

The quinazolin-4-one compound employed in the reaction of the invention as the starting compound is represented by the aforementioned formula (1) In formula (1), each of $R^1$, $R^2$, $R^3$ and $R^4$ a group that can have a substituent, and does not participate in the reactions of the first and second steps For example, the group is a hydrogen atom, an alkyl group having 1-12 carbon atoms, a cycloalkyl group having 1-12 carbon atoms, an aralkyl group having 7-15 carbon atoms, an aryl group having 6-14 carbon atoms, a halogen atom, an alkoxy group having 1-12 carbon atoms, an alkylthio group having 1-12 carbon atoms, an arylthio group having 6-14 carbon atoms, nitro, cyano, amino, carboxyl, ester groups, or amide. $R^1$, $R^2$, $R^3$ and $R^4$ can be combined with each other to form a ring.

Examples of the alkyl groups include methyl, ethyl, propyl, butyl, pentyl, hexyl, heptyl, octyl, nonyl, and decyl. These groups can be any of isomers.

Examples of the cycloalkyl groups include cyclopropyl, cyclobutyl, cyclopentyl, cyclohexyl, cycloheptyl, and cyclooctyl.

Examples of the aralkyl groups include benzyl, phenethyl, and phenylpropyl. These groups can be any of isomers.

Examples of the aryl groups include phenyl, p-tolyl, naphthyl, and anthryl. These groups can be any of isomers.

Examples of halogen atoms include fluorine, chlorine, bromine, and iodine.

Examples of the alkoxy groups include methoxy, ethoxy, and propoxy. These groups can be any of isomers.

Examples of the alkylthio groups include methylthio, ethylthio, and propylthio. These groups can be any of isomers.

Examples of the arylthio groups include phenylthio, p-tolylthio, naphthylthio, and anthrylthio. These groups can be any of isomers.

Examples of the ester groups include methoxycarbonyl, ethoxycarbonyl, and propoxycarbonyl. These groups can be any of isomers.

The above-mentioned alkyl, cycloalkyl, aralkyl, aryl, alkoxy, alkylthio, arylthio, and amino may have a substituent. Examples of the substituents include a substituent bonded via a carbon atom, a substituent bonded via an oxygen atom, a substituent bonded via a nitrogen atom, a substituent bonded via a sulfur atom, and a halogen atom.

Examples of the substituents bonded via a carbon atom include alkyl groups such as methyl, ethyl, propyl, butyl, pentyl, and hexyl; cycloalkyl groups such as cyclopropyl, cyclobutyl, cyclopentyl, and cyclohexyl; alkenyl groups such as vinyl, allyl, propenyl, cyclopropenyl, cyclobutenyl, and cyclopentenyl; heterocyclic alkenyl groups such as pyrrolidyl, pyrrolyl, furyl, and thienyl; aryl groups such as phenyl, tolyl, xylyl, biphenylyl, naphthyl, anthryl, and phenanthryl; acyl groups (possibly be acetallized) such as formyl, acetyl, propionyl, acryloyl, pivaloyl, cyclohexylcarbonyl, benzoyl, naphthoyl, and toluoyl; carboxyl groups; alkoxycarbonyl groups such as methoxycarbonyl and ethoxycarbonyl; aryloxycarbonyl groups such as phenoxycarbonyl; halogenated alkyl groups such as trifluoromethyl; and cyano. These groups can be any of isomers.

Examples of the substituents bonded via an oxygen atom include hydroxyl; alkoxy groups such as methoxy, ethoxy, propoxy, butoxy, pentyloxy, hexyloxy, heptyloxy, benzyloxy, piperidyloxy, and pyranyloxy; and aryloxy groups such as phenoxy, toluoyloxy, and naphthyloxy. These groups can be any of isomers.

Examples of the substituents bonded via a nitrogen atom include primary amino groups such as methylamino, ethylamino, butylamino, cyclohexylamino, phenylamino, and naphthylamino; secondary amino groups such as dimethylamino, diethylamino, dibutylamino, methylethylamino, methylbutylamino, and diphenylamino; heterocyclic amino groups such as morpholino, piperidino, piperazinyl, pyrazolidinyl, pyrrolidino, and indolyl; and imino. These groups can be any of isomers.

Examples of the substituents bonded via a sulfur atom include mercapto; thioalkoxy groups such as thiomethoxy, thioethoxy, and thiopropoxy; and thioaryloxy groups such as thiophenoxy, thiotoluoyloxy, and thionaphthyloxy. These groups can be any of isomers.

Examples of the halogen atoms include fluorine, bromine, and iodine.

$R^5$ is a hydrogen atom or a hydrocarbyl group which can have a substituent. Examples of the hydrocarbyl groups include alkyl groups having 1-12 carbon atoms such as methyl, ethyl, propyl, butyl, pentyl, and hexyl; cycloalkyl groups such having 1-12 carbon atoms as cyclopropyl, cyclobutyl, cyclopentyl, and cyclohexyl; aralkyl groups having 7-13 carbon atoms such as benzyl, phenethyl, and phenylpropyl; and aryl groups having 7-13 carbon atoms such as phenyl, tolyl, naphthyl, and anthryl. These groups can be any of isomers.

The above-mentioned hydrocarbyl group can have a substituent. Examples of the substituents are those described for $R^1$, $R^2$, $R^3$ and $R^4$.

The organic base used in the reaction of the first step can be an aliphatic amine such as trimethylamine, triethylamine, ethyldiisopropylamine, or tributylamine; an aromatic amine such as dimethylaniline or diethyl aniline; or a heterocyclic amine such as pyridine, quinoline, pyrimidine, or 4-dimethylaminopyridine. Preferred is an aliphatic amine. More preferred is triethylamine. The organic base can be used singly or in combination.

The organic base can be employed preferably in an amount of 0.3 to 2.5 moles, more preferably 1.0 to 1.5 moles, per one mole of the quinazolin-4-one compound.

There are no specific limitations with respect to the organic solvent employed in the reaction of the first step, so far as the solvent does not participate in the reaction. Examples are aliphatic hydrocarbons such as hexane, cyclohexane, and heptane; halogenated hydrocarbons such as chloroform and dichloroethane; aromatic hydrocarbons such as toluene, xylene, and mesitylene; halogenated aromatic hydrocarbons such as chlorobenzene, ethers such as diethyl ether, tetrahydrofuran, and dimethoxyethane; and amides such as N,N-dimethylformamide and 1,3-dimethylimidazolindione. Preferred are aromatic hydrocarbons. More preferred is toluene. The organic solvents can be employed singly or in combination. Further, the organic solvent can be placed in the reaction mixture while the reaction proceeds, if necessary.

The amount of the organic solvent employed in the reaction depends on the homogeneity and stirring condition of the reaction mixture. It is preferred that the solvent is employed in an amount of 0.5 to 30 g (more preferably 1 to 10 g, most preferably 1 to 5 g) per one gram of the quinazolin-4-one compound.

The chlorinating agent used in the reaction of the first step can be phosphorus oxychloride, phosphorus trichloride, phosphorus pentachloride, thionyl chloride, sulfuryl chloride, nitrosyl chloride, and chlorine molecule. Preferred is phosphorus oxychloride. The chlorinating agent can be used singly or in combination.

The chlorinating agent is preferably employed in an amount of 0.9 to 7.0 moles, more preferably 1.0 to 5.0 moles, most preferably 1.0 to 2.5 moles per one mole of the quinazolin-4-one compound.

There are no specific limitations with respect to the organic solvent employed in the reaction of the second step, so far as the solvent does not participate in the reaction. Examples of the organic solvents include halogenated aliphatic hydrocarbons such as methylene chloride and chloroform; halogenated aromatic hydrocarbons such as chlorobenzene; nitriles such as acetonitrile and propionitrile; ketones such as acetone, methyl ethyl ketone, methyl isopropyl ketone, and methyl isobutyl ketone; and ethers such as diethyl ether, tetrahydrofuran, and dimethoxyethane. Preferred are ketones. More preferred is methyl ethyl ketone. The organic solvent can be used singly or in combination.

The amount of the organic solvent employed in the reaction depends on the homogeneity and stirring condition of the reaction mixture. It is preferred that the solvent is employed in an amount of 0.1 to 10 mL (more preferably 0.5 to 5 mL) per one gram of the quinazolin-4-one compound.

The amine compound used in the reaction of the second step of the invention is represented by the aforementioned formula (2).

The reactions of the process of the invention can be performed, for instance, by a first step in which a quinazolin-4-one compound, an organic base, a chlorinating agent, and an organic solvent are mixed and stirred in an inert gas atmosphere, and a second step in which the resulting reaction liquid is further stirred after addition of an organic solvent and an amine compound. These reactions are preferably carried out at a temperature in the range of 10 to 150° C., more preferably 50 to 120° C., most preferably 40 to 100° C. There are no specific limitations with respect to the reaction pressure.

The combination of the first and second steps can give the main product, i.e., hydrochloride of a 4-aminoquinazoline compound, which can be neutralized with a base (e.g., aqueous alkali metal hydroxide) to give a free 4-aminoquinazoline compound.

The 4-aminoquinazoline compound produced in the second step can be isolated and purified by the conventional procedures such as filtration, extraction, concentration, distillation, recrystallization, and column chromatography.

As described above, 6-halogeno-4-arylaminoquinazoline of formula (6) can be obtained by employing 6-halogenoquinazolin-4-one of formula (4) as the quinazolin-4-one compound and arylamine of formula (5) as the amine compound.

In formulas (4) and (6), X is a halogen atom (fluorine, chlorine, bromine, or iodine). Preferred is iodine. Ar in formulas (5) and (6) is an aryl group that can have a substituent Examples of the aryl groups are carbon ring aromatic groups having 6-14 carbon atoms and heterocyclic aromatic groups such as phenyl, biphenylyl, naphthyl, anthryl, phenanthryl, pyridyl, quinolyl, pyrrolidyl, pyrrolyl, furyl, and thienyl.

Examples of the substituents are substituents bonded via carbon atom, substituents bonded via oxygen atom, substituents bonded via nitrogen atom, substituents bonded via sulfur atom, and halogen atoms. There are no limitations with respect to number and position of the substituent.

When the compound of formula (4) and the compound of formula (6) are employed as the starting compounds, 6 halogeno-4-arylaminoquinazoline hydrochloride is produced as a main product after the second step. This product can be converted to free 6-halogeno-4-arylaminoquinazoline by neutralization with a base (e.g., aqueous alkali metal hydroxide). Thus obtained 6-halogeno-4-arylaminoquinazoline can be isolated and purified by the conventional procedures such as filtration, extraction, concentration, distillation, recrystallization, and column chromatography.

When 6-halogenoquinazolin-4-one of formula (4) is employed as the starting compound in the first step, the main reaction product, i.e., 6-halogeno-4-chloroquinazoline can be isolated before it is processed in the second step.

6-Halogeno-4-chloroquinazoline can be recovered as a crystalline product, for instance, by cooling the reaction liquid. However, it is preferred that the reaction liquid is stirred preferably at −10-70° C., more preferably at 0-30° C., after addition of an organic solvent, whereby a crystalline product precipitates.

The organic solvent can be halogenated aliphatic hydrocarbon such as methylene chloride or chloroform; halogenated aromatic hydrocarbon such as chlorobenzene; nitriles such as acetonitrile or propionitrile, ketone such as acetone, methyl ethyl ketone, methyl isopropyl ketone, or methyl isobutyl ketone; or ether such as diethyl ether, tetrahydrofuran, or dimethoxyethane. Preferred is ketone. More preferred is methyl ethyl ketone. The organic solvent can be used singly or in combination.

The amount of the organic solvent depends on the homogeneity and stirring condition of the reaction mixture. It is preferred that the organic solvent is employed in an amount of 0.1 to 10 mL (more preferably 0.5 to 5 mL) per one gram of the 6-halogenoquinazolin-4-one.

The crystalline product of 6-halogeno-4-chloroquinazoline can be further purified by stirring the product in aqueous alkali metal hydroxide to remove impurities (e.g., organic base hydrochloride).

Example I-1

Preparation of 4-(3-chloro-4-fluoro)-anilinoquinazoline

In a 20 mL-volume glass vessel equipped with a stirrer, a thermometer and a reflux condenser were placed 0.80 g (5.5 mmol) of quinazolin-4-one, 1.00 g (6.6 mmol) of phosphorus oxychloride, and 10 mL of toluene in a nitrogen atmosphere. While the mixture was stirred at room temperature, 0.66 g (6.6 mmol) of triethylamine was slowly added. The resulting mixture was heated to 75° C. and then reaction was carried out for 2 hours. Subsequently, the mixture was cooled to room temperature, and 1.6 mL of methyl isobutyl ketone and 0.96 g (6.6 mmol) of 3-chloro-4-fluoroaniline were added. The resulting mixture was again heated to 75° C., and then reaction was carried out under stirring for one hour. After the reaction was complete, the reaction mixture was cooled to room temperature, and thus precipitated crystalline product was collected by filtration. Subsequently, the crystal line product was placed in 30 mL of aqueous sodium hydroxide (1 mol/L), and the aqueous mixture was stirred for 30 minutes at room temperature. The crystalline product was collected by filtration, washed with 30 mL of water, and dried under reduced pressure, to give 1.35 g (isolated yield: 89%, purity 99% in terms of area percentage determined by high performance liquid chromatography) of 4-(3-chloro-4-fluoro)anilinoquinazoline as a yellowish crystalline product.

4-(3-Chloro-4-fluoro)anilinoquinazoline had the following physical properties.

$^1$H-NMR (DMSO-$d_6$, δ (ppm)): 7.46 (1H, t, J=9.0 Hz), 7.64-7.70 (1H, m), 7.81-7.92 (3H, m), 8.23 (1H, dd, J=6.6, 2.4 Hz), 8.53 (1H, d, J=8.1 Hz), 8.66 (1H, s), 9.90 (1H, s)

CI-MS (m/e): 274 (M+1)

Example I-2

Preparation of 6-methyl-4-(3-chloro-4-methoxy)anilinoquinazoline

In a 20 mL-volume glass vessel equipped with a stirrer, a thermometer and a reflux condenser were placed 0.80 g (5.0 mmol) of 6-methylquinazolin-4-one, 0.92 g (6.0 mmol) of phosphorus oxychloride, and 5 mL of toluene in a nitrogen atmosphere. While the mixture was stirred at room temperature, 0.61 g (6.0 mmol) of triethylamine was slowly added. The resulting mixture was heated to 75° C., and then reaction was carried out for 2 hours. Subsequently, the mixture was cooled to room temperature, and 1.6 mL of methyl isobutyl ketone and 0.94 g (6.0 mmol) of 3-chloro-4-methoxyaniline were added. The resulting mixture was again heated to 75° C. and then reaction was carried out under stirring for one hour. After the reaction was complete, the reaction mixture was cooled to room temperature, and thus precipitated crystalline product was collected by filtration. Subsequently, the crystalline product was placed in 30 mL of aqueous sodium hydroxide (1 mol/L), and the aqueous mixture was stirred for 30 minutes at room temperature. The crystalline product was collected by filtration, washed with 30 mL of water, and dried under reduced pressure, to give 1.36 g (isolated yield: 91%, purity 99% in terms of area percentage determined by high performance liquid chromatography) of 6-methyl-4-(3-chloro-4-methoxy)anilinoquinazoline as a yellowish crystalline product.

6-Methyl-4-(3-chloro-4-methoxy)anilinoquinazoline had the following physical properties.

$^1$H-NMR (DMSO-$d_6$, δ (ppm)): 3.87 (3H, d, J=9.0 Hz), 7.47 (1H, dd, J=8.7, 1.8 Hz), 7.58 (1H, s), 7.75 (1H, dd, J=9.0, 2.4 Hz), 8.03 (1H, d, J=2.7 Hz), 8.40 (1H, d, J=8.4 Hz), 8.55 (1H, s), 9.68 (1H, s)

CI-MS (m/e): 300 (M+1)

Example I-3

Preparation of 6-iodo-4-benzylamino-quinazoline

In a 20 ml-volume glass vessel equipped with a stirrer, a thermometer and a reflux condenser were placed 2.0 g (7.4 mmol) of 6-iodoquinazolin-4-one) 1.35 g (8.8 mmol) of phosphorus oxychloride, and 10 mL of toluene in a nitrogen atmosphere. While the mixture was stirred at room temperature, 0.66 g (6.6 mmol) of triethylamine was slowly added. The resulting mixture was heated to 75° C., and then reaction was carried out for 2 hours. Subsequently, the mixture was cooled to room temperature, and 3 mL of methyl isobutyl ketone and 3.15 g (29.4 mmol) of benzylamine were added. The resulting mixture was again heated to 75° C., and then reaction was carried out under stirring for one hour. After the reaction was complete, the reaction mixture was cooled to room temperature. Thus precipitated crystalline product was collected by filtration. Subsequently, the crystalline product was placed in 30 mL of aqueous sodium hydroxide (1 mol/L), and the aqueous mixture was stirred for 30 minutes at room temperature. The crystalline product was collected by filtration, washed with 30 mL of water, and dried under reduced pressure, to give 2.26 g (isolated yield: 84%, purity 99% in terms of area percentage determined by high performance liquid chromatography) of 6-iodo-4-benzyl-aminoquinazoline as a yellowish crystalline product.

6-Iodo-4-benzylaminoquinazoline had the following physical properties.

$^1$H-NMR (DMSO-$d_6$, δ (ppm)): 4.77 (2H, d, J=5.7 Hz), 7.22-7.39 (5H, m), 7.47 (1H, d, J=8.7 Hz), 8.03 (1H, dd, J=9.0, 1.8 Hz), 8.48 (1H, s), 8.80 (1H, d, J=1.5 Hz), 8.99 (1H, t, J=5.4 Hz)

CI-MS (m/e): 362 (M+1)

Example I-4

Preparation of 6-iodo-4-piperidino-quinazoline

The procedures of Example I-3 were repeated except for replacing benzylamine with 1.13 g (13.3 mmol) of piperidine, to give 2.26 g (isolated yield: 79%, purity 87% in terms of area percentage determined by high performance liquid chromatography) of 6-iodo-4-piperidino-quinazoline as a yellowish crystalline product.

6-Iodo-4-piperidinoquinazoline had the following physical properties.

$^1$H-NMR (DMSO-$d_6$, δ (ppm)): 1.6-1.7 (6H, m), 3.6-3.7 (4H, m), 7.56 (1H, d, J=8.7 Hz), 8.04 (1H, dd, J=8.7, 1.8 Hz), 8.21 (1H, d, J=1.8 Hz), 8.60 (1H, s)

CI-MS (m/e): 340 (M+1)

Example II-1

Preparation of 6-iodo-4-anilinoquinazoline

In a 20 mL-volume glass vessel equipped with a stirrer, a thermometer and a reflux condenser were placed 2.00 g (7.35 mmol) of 6-iodoquinazolin-4-one, 1.35 g (8.8 mmol) of phosphorus oxychloride, and 6 mL of toluene in a nitrogen atmosphere. While the mixture was stirred at room temperature, 0.89 g (8.8 mmol) of triethylamine was slowly added. The resulting mixture was heated to 75° C., and then reaction was carried out for 2 hours. Subsequently, the mixture was cooled to room temperature, and 3 mL of acetone and 821 mg (8.8 mmol) of aniline were added. The resulting mixture was again heated to 75° C., and then reaction was carried out under stirring for one hour. After the reaction was complete, the reaction mixture was cooled to room temperature, and thus precipitated crystalline product was collected by filtration. Subsequently, the crystalline product was placed in 30 mL of aqueous sodium hydroxide (1 mol/L), and the aqueous mixture was stirred for 30 minutes at room temperature. The crystalline product was collected by filtration, washed with 30 mL of water, and dried under reduced pressure, to give 1.91 g (isolated yield: 73%, purity 97% in terms of area percentage determined by high performance liquid chromatography) of 6-iodo-4-anilinoquinazoline as a yellowish crystalline product.

6-Iodo-4-anilinoquinazoline had the following physical properties.

$^1$H-NMR (DMSO-$d_6$, δ (ppm)); 7.12-7.18 (1H, m), 7.37-7.44 (2H, m), 7.56 (1H, d, J=8.7 Hz), 7.82-7.88 (2H, m) 8.12 (1H, dd, J=2.1, 8.7 Hz), 8.61 (1H, s), 9.01 (1H, d, J=1.8 Hz), 9.87 (1H, s)

CI-MS (m/e): 348 (M+1)

Example II-2

Preparation of 6-iodo-4-anilinoquinazoline

The procedures of Example II-1 were repeated except that acetone was replaced with methyl isobutyl ketone and that 753 mg (8.1 mmol) of aniline was used, to give 1.90 g (isolated yield: 74%, purity 99% in terms of area percentage determined by high performance liquid chromatography) of 6-iodo-4-anilinoquinazoline.

Example II-3

Preparation of 6-iodo-4-(3-chloro-4-methoxy)anilinoquinazoline

The procedures of Example II-1 were repeated except for replacing aniline with 1.39 g (8.8 mmol) of 3-chloro-4-methoxyaniline, to give 2.92 g (isolated yield: 96%, purity 96% in terms of area percentage determined by high performance liquid chromatography) of 6-iodo-4-(3-chloro-4-methoxy)anilinoquinazoline as a yellowish crystalline product.

6-Iodo-4-(3-chloro-4-methoxy)anilinoquinazoline had the following physical properties.

$^1$H-NMR (DMSO-$d_6$, δ (ppm)): 3.88 (3H, s), 7.20 (1H, d, J=9.3 Hz), 7.55 (1H, d, J=8.7 Hz), 7.75 (1H, dd, J=2.7, 9.0 Hz), 8.00 (1H, d, J=2.7 Hz), 8.10 (1H, dd, J=2.1, 8.7 Hz), 8.61 (1H, s), 8.96 (1H, d, J=1.8 Hz), 9.83 (1H, s)

CI-MS (m/e): 412 (M+1)

Example II-4

Preparation of 6-iodo-4-(3-chloro-4-methoxy)anilinoquinazoline

In a 500 mL-volume glass vessel equipped with a stirrer, a thermometer and a reflux condenser were placed 51.7 g (190 mmol) of 6-iodoquinazolin-4-one, 35.0 g (228 mmol) of phosphorus oxychloride, and 153 mL of toluene in a nitrogen atmosphere. While the mixture was stirred at room temperature, 23.1 g (228 mmol) of triethylamine was slowly added. The resulting mixture was heated to 75° C., and then reaction was carried out for 2 hours. Subsequently, the mixture was cooled to room temperature, and 51 mL of methyl ethyl ketone was added. The resulting mixture was stirred for 10 minutes. Then, the mixture was again heated to 75° C., while 40.0 g (228 mmol) of 3 chloro-4-methoxyaniline was slowly added. The resulting mixture was stirred for 2 hours at the same temperature after addition of 250 mL of toluene and 150 mL of methyl ethyl ketone. After the reaction was complete, the reaction mixture was cooled to room temperature, and thus precipitated crystalline product was collected by filtration. Subsequently, the crystalline product was placed in 300 mL of aqueous sodium hydroxide (1 mol/L), and the aqueous mixture was stirred for 30 minutes at room temperature. The crystalline product was collected by filtration, washed with 500 mL of waters and dried under reduced pressure, to give 73.4 g (isolated yield: 94%, purity 99.5% in terms of area percentage determined by high performance liquid chromatography) of 6-iodo-4-(3-chloro-4-methoxy)anilinoquinazoline as a yellowish crystalline product.

Example II-5

Preparation of 6-iodo-4-(3-chloro-4-methoxy)anilinoquinazoline

The procedures of Example II-3 were repeated except that acetone was replaced with methyl isobutyl ketone and that 1.28 g (8.1 mmol) of 3-chloro-4-methoxyaniline was used, to give 2.55 g (isolated yield: 84%, purity 99% in terms of area percentage determined by high performance liquid chromatography) of 6-iodo-4-(3-chloro-4-methoxy)anilinoquinazoline.

Example II-6

Preparation of 6-iodo-4-(3-chloro-4-fluoro)anilinoquinazoline

The procedures of Example II-1 were repeated except that acetone was replaced with methyl isobutyl ketone and that aniline was replaced with 1.18 g (8.1 mmol) of 3-chloro-4-fluoroaniline, to give 2.45 g (isolated yield: 83%, purity 99% in terms of area percentage determined by high performance liquid chromatography) of 6-iodo-4-(3-chloro-4-fluoro)anilinoquinazoline as a pale yellow crystalline product.

6-Iodo-4-(3-chloro-4-fluoro)anilinoquinazoline had the following physical properties.

$^1$H-NMR (DMSO-$d_6$, δ (ppm)): 7.46 (1H, t, J=9.0 Hz) 7.59 (1H, d, J=8.7 Hz), 7.82-7.87 (1H, m), 8.12-8.21 (2H, m), 8.66 (1H, s), 8.96 (1H, d, J=2.1 Hz), 9.95 (1H, s)

CI-MS (m/e): 400 (M+1)

Example III-1

Preparation of 6-iodo-4-[3-chloro-4-(3-fluorobenzyloxy)anilino]quinazoline

In a 200 mL-volume glass vessel equipped with a stirrer, a thermometer and a reflux condenser were placed 9.80 g (36 mmol) of 6-iodoquinazolin-4-one, 6.63 g (43 mmol) of phosphorus oxychloride, and 30 mL of toluene in a nitrogen atmosphere. While the mixture was stirred at room temperature, 4.41 g (8.8 mmol) of triethylamine was slowly added. The resulting mixture was heated to 75° C., and then reaction was carried out at 70-80° C. for 3 hours. Subsequently, the mixture was cooled to room temperature, and 40 mL of acetonitrile and 11.8 mg (43 mmol) of 3-chloro-4-(3-fluorobenzyloxy) aniline were added. The resulting mixture was stirred at 70-80° C. for 2 hours. After the reaction was complete, the reaction mixture was cooled to room temperature, and thus precipitated crystalline product was collected by filtration and washed with 20 mL of acetonitrile. Subsequently, the crystalline product was placed in 80 mL of aqueous sodium hydroxide (1 mol/L), and the aqueous mixture was stirred for 2 hours at room temperature. The crystalline product was collected by filtration, washed with 500 mL of water and 20 mL of acetonitrile, and dried under reduced pressure, to give 18.0 g (isolated yield: 98%, purity 100% in terms of area percentage determined by high performance liquid chromatography) of 6-iodo-4-[3-chloro-4-(3-fluorobenzyloxy)anilino]quinazoline as a yellowish crystalline product.

6-Iodo-4-[3-chloro-4-(3-fluorobenzyloxy)anilino]quinazoline had the following physical properties.

$^1$H-NMR (DMSO-$d_6$, δ (ppm)): 5.26 (2H, s), 7.16-7.22 (1H, m), 7.26-7.35 (3H, m), 7.44-7.51 (1H, m), 7.56 (1H, d, J=8.8 Hz), 7.75 (1H, dd, J=9.0, 2.4 Hz), 8.03 (1H, s), 8.12 (1H, d, J=8.8 Hz), 8.61 (1H, s), 8.96 (1H, s), 9.85 (1H, s)

CI-MS (m/e): 506 (M+1)

Example III-2

Preparation of 6,7-bis(2-methoxyethoxy)-4-(3-ethynylanilino)quinazoline Hydrochloride In a 50 mL-volume glass vessel equipped with a stirrer, a thermometer and a reflux condenser were placed 4.08 g (13.9 mmol) of 6,7-bis(2-methoxy)quinazolin-4-one, 2.55 g (16.7 mmol) of phosphorus oxychloride, 3.37 g (33.4 mmol) of triethylamine and 12 mL of toluene in a nitrogen atmosphere. The resulting mixture was heated at 70-80° C. for 3 hours. Subsequently the mixture was cooled to room temperature, and 1.94 g (16-7 mmol) of 3-ethynylaniline was added. The resulting mixture was then stirred at 70-80° C. for 2 hours. Subsequently, the mixture was stirred at room temperature after addition of 16 mL of acetonitrile. After the reaction was complete, the precipitated crystalline product was collected by filtration, washed with 8 mL of cooled acetonitrile, and dried under reduced pressure, to give 6.75 g (isolated yield: 88%, purity 78.1% in terms of area percentage determined by high performance liquid chromatography) of 6,7-bis(2-methoxyethoxy) 4-(3-ethynylanilino)quinazoline hydrochloride as yellow solid.

6,7-Bis(2-methoxyethoxy)+4-(3-ethynylanilino)quinazoline hydrochloride had the following physical properties.

$^1$H-NMR (DMSO-$d_6$, δ (ppm)): 3.63 (2H, s), 3.78-3.80 (4H, m), 4.28 (1H, s), 4.33-4.41 (4H, m), 7.39-7.52 (3H, m), 7.80 (1H, d, J=8.1 Hz), 7.89 (1H, s), 8.46 (1H, s), 8.85 (1H, brs), 11.60 (1H, s), 14.9 (1H, brs)

CI-MS (m/e): 394 (M+1)

Example III-3

Preparation of 4-(3-chloro-4-fluoro-anilino)-6-methoxy-7-(3-morpholinopropoxy)quinazoline In a 50 mL-volume glass vessel equipped with a stirrer, a thermometer and a reflux condenser were placed 2.00 g (6.3 mmol) of 6-methoxy-7-(3-morpholinopropoxy)quinazolin-4-one, 1.19 g (7.6 mmol) of phosphorus oxychloride, 0.76 g (6.3 mmol) of triethylamine, and 8 mL of toluene in a nitrogen atmosphere. The mixture was then stirred at 70-80° C. for 3 hours. Subsequently, the mixture was cooled to room temperature, and 1.09 g (6.3 mmol) of 3-chloro-4-fluoroaniline and 6 mL of toluene were added. The resulting mixture was stirred at 110° C. for 10 hours, Further, the mixture was stirred at room temperature after addition of 8 mL of acetonitrile. After the reaction was complete, the precipitated crystalline product was collected by filtration, and washed with 5 mL of cooled acetonitrile. Subsequently, the crystalline product was placed in 16 mL of aqueous sodium hydroxide (1 mol/L), and the aqueous mixture was stirred for 4 hours at room temperature. The crystalline product was collected by filtration, washed with 50 mL of water and 5 mL of acetonitrile, and dried under reduced pressure, to give 2.28 g (isolated yield: 71%, purity 89% in terms of area percentage determined by high performance liquid chromatography) of 4-(3-chloro-4-fluoroanilino)-6-methoxy-7-(3-morpholinopropoxy)quinazoline as a sallowish crystalline product.

4-(3-Chloro-4-fluoroanilino)-6-methoxy-7-(3-morpholinopropoxy)quinazoline had the following physical properties.

$^1$H-NMR (DMSO-$d_6$, δ (ppm)): 1.93-2.00 (2H, m), 2.36-2.51 (6H, m), 3.57-3.60 (4H, m), 3.97 (3H, s), 4.19-4.21 (2H, m), 7.20 (1H, s), 7.42-7.48 (1H, m), 7.78-7.84 (2H, m), 8.13 (1H, dd, J=6.8, 2.7 Hz), 8.50 (1H, s), 9.56 (1H, s)

CI-MS (m/e): 447 (M+1)

Example IV-1

Preparation of 6-iodo-4-chloroquinazoline

In a 100 mL-volume glass vessel equipped with a stirrer, a thermometer and a reflux condenser were placed 20.0 g (73.5 mmol) of 6-iodoquinazolin-4-one, 13.5 g (88.2 mmol) of phosphorus oxychloride, and 60 mL of toluene in a nitrogen atmosphere. While the mixture was stirred at room temperature, 8.92 g (88.2 mmol) of triethylamine was slowly added. The resulting mixture was heated to 75° C., and the reaction was carried out for 2 hours. After the reaction was complete, the reaction mixture was cooled to 0° C. and stirred for one hour. Thus precipitated pale yellow crystalline product of 6-iodo-4-chloroquinazoline was collected by filtration. Subsequently, the crystalline product was placed in 100 mL of aqueous sodium hydroxide (1 mol/L), and the aqueous mixture was stirred for 30 minutes at room temperature. The crystalline product was collected by filtration, washed with 120 mL of water, and dried under reduced pressure, to give 19.3 g (isolated yield: 90%, purity 99.3% in terms of area percentage determined by high performance liquid chromatography) of 6-iodo-4-chloroquinazoline as a yellowish crystalline product.

The analysis of 6-halogeno-4-chloroquinazoline in the reaction mixture was performed by the following procedures: After the reaction was complete, 6-halogeno-4-chloroquinazoline was reacted with methanol to give 6-halogeno-4-methoxyquinazoline quantitatively, which was then analyzed by high performance liquid chromatography.

6-Iodo-4-chloroquinazoline had the following physical properties.

$^1$H-NMR (CDCl$_3$, δ (ppm)): 7.80 (1H, d, J=7.8 Hz), 8.20 (1H, dd, J=2.1, 9.0 Hz), 8.65 (1H d, J=2.1 Hz), 9.06 (1H, s)

CI-MS (m/e): 291 (M+1)

Example IV-2

Preparation of 6-iodo-4-chloroquinazoline

In a 20 mL-volume glass vessel equipped with a stirrer, a thermometer and a reflux condenser were placed 2.00 g (7.35 mmol) of 6-iodoquinazolin-4-one, 1.24 g (8.09 mmol) of phosphorus oxychloride, and 10 mL of toluene in a nitrogen atmosphere. While the mixture was stirred at room temperature, 0.82 g (8.09 mmol) of triethylamine was slowly added. The resulting mixture was heated to 75° C., and the reaction was carried out for 2 hours. After the reaction was complete, the reaction mixture was cooled to room temperature, and 100 mL of methanol was added. The mixture was stirred for 15 minutes at the same temperature, to give 6-iodo-4-methoxyquinazoline. Analysis of the reaction mixture by high performance liquid chromatography indicated that 2.11 g (reaction yield: 99%) of 6-iodo-4-chloroquinazoline was produced.

Example IV-3

Preparation of 6-iodo-4-chloroquinazoline

The procedures of Example IV-2 were repeated except that 1-80 g (11.8 mmol) of phosphorus oxychloride was used and that 1.19 g (11.8 mmol) of triethylamine was used. There was produced 2.11 g (reaction yield: 99%) of 6-iodo-4-chloroquinazoline.

Example IV-4

Preparation of 6-iodo-4-chloroquinazoline

The procedures of Example IV-2 were repeated except that 2.48 g (16.2 mmol) of phosphorus oxychloride was used and that 1.64 g (16.2 mmol) of triethylamine was used. There was produced 2.14 g (reaction yield: 1003) of 6-iodo-4-chloroquinazoline.

Example IV-5

Preparation of 6-iodo-4-chloroquinazoline

The procedures of Example IV-2 were repeated except that the reaction temperature was changed to 55° C. There was produced 2.05 g (reaction yield: 96%) of 6-iodo-4-chloroquinazoline.

Example IV-6

Preparation of 6-iodo-4-chloroquinazoline

The procedures of Example IV-2 were repeated except that the reaction temperature was changed to 95° C. There was produced 2.09 g (reaction yield: 98%) of 6-iodo-4-chloroquinazoline.

Example IV-7

Preparation of 6-iodo-4-chloroquinazoline

The procedures of Example IV-4 were repeated except for replacing triethylamine with 1.96 g (16.2 mmol) of N,N-dimethylaniline. There was produced 1.92 g (reaction yield: 90%) of 6-iodo-4-chloroquinazoline.

Example IV-8

Preparation of 6-iodo-4-chloroquinazoline

The procedures of Example IV-4 were repeated except for replacing triethylamine with 1.28 g (16.2 mmol) of pyridine. There was produced 1.96 g (reaction yield: 92%) of 6-iodo-4-chloroquinazoline.

Example IV-9

Preparation of 6-iodo-4-chloroquinazoline

In a 500 mL-volume glass vessel equipped with a stirrer, a thermometer and a reflux condenser were placed 50.0 g (184 mmol) of 6-iodoquinazolin-4-one, 33.8 g (221 mmol) of phosphorus oxychloride, and 300 mL of toluene in a nitrogen atmosphere. While the mixture was stirred at room temperature, 22.3 g (221 mmol) of triethylamine was slowly added. The resulting mixture was heated at 60° C. for 30 minutes and then heated at 75° C. for 2 hours, for carrying out reaction. After the reaction was complete, the reaction mixture was cooled to room temperature, and 50 mL of acetone was added. The mixture was then cooled to 0° C. and stirred for 30 minutes. Thus precipitated pale yellow crystalline product of 6-iodo-4-chloroquinazoline was collected by filtration. Subsequently, the crystalline product was placed in 200 mL of water, and 9 mL of aqueous sodium hydroxide (1 mol/L) was added. The aqueous mixture (pH 10-11) was stirred for 30 minutes at room temperature. The crystalline product was collected by filtration, washed successively with 100 mL of acetone, 200 mL of water and 100 mL of acetone, and dried at 60° C. under reduced pressure, to give 47.4 g (isolated yield: 89%, purity 99% in terms of area percentage determined by high performance liquid chromatography) of 6-iodo-4-chloroquinazoline as a yellowish crystalline product.

Example IV-10

Preparation of 6-iodo-4-chloroquinazoline

The procedures of Example IV-9 were repeated except for replacing acetone with methyl ethyl ketone. There was produced 44.9 g (isolated yield: 84%) of 6-iodo-4-chloroquinazoline.

Example IV-11

Preparation of 6-iodo-4-chloroquinazoline

The procedures of Example IV-9 were repeated except for replacing acetone with methyl isopropyl ketone. There was produced 48.6 g (isolated yield: 91%) of 6-iodo-4-chloroquinazoline.

Example IV-12

Preparation of 6-iodo-4-chloroquinazoline

The procedures of Example IV-9 were repeated except for replacing acetone with acetonitrile. There was produced 48.1 g (isolated yield: 90%) of 6-iodo-4-chloro quinazoline.

Example IV-13

Preparation of 6-iodo-4-chloroquinazoline

The procedures of Example IV-9 were repeated except for replacing acetone with chloroform. There was produced 48.1 g (isolated yield: 90%) of 6-iodo-4-chloroquinazoline.

Example IV-14

Preparation of 6-iodo-4-chloroquinazoline

The procedures of Example IV-9 were repeated except for replacing acetone with tetrahydrofuran. There was produced 47.6 g (isolated yield: 89%) of 6-iodo-4-chloroquinazoline.

Example IV-15

Preparation of 6-iodo-4-chloroquinazoline

The procedures of Example IV-1 were repeated except for replacing toluene with chlorobenzene There was produced 48.1 g (isolated yield: 90%) of 6-iodo-4-chloroquinazoline.

Example IV-16

Preparation of 6-iodo-4-chloroquinazoline

The procedures of Example IV-1 were repeated except that the stirring temperature after completion of the reaction was changed from 0° C. to 25° C. There was produced 45.4 g (isolated yield: 85%) of 6-iodo-4-chloroquinazoline.

Example IV-17

Preparation of 6-iodo-4-chloroquinazoline

The procedures of Example IV-10 were repeated except that the stirring temperature after completion of the reaction was changed from 0° C. to 25° C. There was produced 44.9 g (isolated yield: 84%) of 6-iodo-4-chloroquinazoline.

Example IV-18

Preparation of 6-iodo-4-chloroquinazoline

The procedures of Example IV-9 were repeated except that acetone was replaced with methyl isopropyl ketone and that the stirring temperature after completion of reaction was changed from 0° C. to 25° C. There was produced 47.0 g (isolated yield: 88%) of 6-iodo-4-chloroquinazoline.

Example IV-19

Preparation of 6-iodo-4-chloroquinazoline

The procedures of Example TV-9 were repeated except that acetone was replaced with methyl isobutyl ketone and that the stirring temperature after completion of reaction was changed from 0° C. to 25° C. There was produced 44.9 g (isolated yield: 84%) of 6-iodo-4-chloroquinazoline.

UTILIZATION IN INDUSTRY

According to the invention, 4-aminoquinazoline compounds can be produced from quinazolin-4-one compounds by simple procedures. Further, 6-halogeno-4-arylaminoquinazoline can be produced from 6-halogenoquinazolin-4-one by simple procedures. Furthermore, the invention provides processes for producing 6-iodo-4-[3-chloro-4-(3-fluorobenzyloxy)anilino]quinazoline, 6,7-bis(2-methoxyethoxy)-4-(3-ethynylanilino)quinazoline, and 4-(3-chloro-4-fluoroanilino)-6-methoxy-7-(3-morpholinopropoxy)quinazoline. These compounds are of value as intermediate compounds for preparing pharmaceuticals showing excellent pharmacological functions.

What is claimed is:

1. A process for preparing a 4-aminoquinazoline compound having the formula (3):

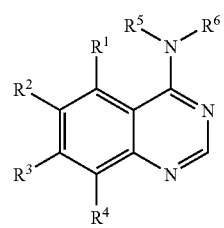

(3)

in which each of $R^1$, $R^2$, $R^3$ and $R^4$ independently represents a group selected from the group consisting of a hydrogen atom, an alkyl group having 1-12 carbon atoms, a cycloalkyl group having 1-12 carbon atoms, an aralkyl group having 7-15 carbon atoms, an aryl group having 6-14 carbon atoms, a halogen atom, an alkoxy group having 1-12 carbon atoms, an alkylthio group having 1-12 carbon atoms, an arylthio group having 6-14 carbon atoms, nitro, cyano, amino, carboxyl, ester, or amide, in which the alkyl, cycloalkyl, aralkyl, aryl, alkoxy, alkylthio, arylthio, and amino may have a substituent which is selected from the group consisting of alkyl, cycloalkyl, aryl, carboxyl, alkoxycarbonyl, aryloxycarbonyl, halogenated alkyl, cyano, alkoxy, benzyloxy, piperidyloxy, pyranyloxy, aryloxy, secondary amino, heterocyclic amino, thioalkoxy, thioaryloxy, and halogen, or $R^1$, $R^2$, $R^3$ and $R^4$ are combined to form a ring; $R^5$ represents a hydrogen atom or a hydrocarbyl group which can have a substituent which is selected from the group consisting of alkyl, cycloalkyl, aryl, carboxyl, alkoxycarbonyl, aryloxycarbonyl, halogenated alkyl, cyano, alkoxy, benzyloxy, piperidyloxy, pyranyloxy, aryloxy, secondary amino, heterocyclic amino, thioalkoxy, thioaryloxy, and halogen; and $R^6$ is a hydrogen atom or a hydrocarbyl group, which comprises:

a first step of reacting a quinazolin-4-one compound having the formula (1):

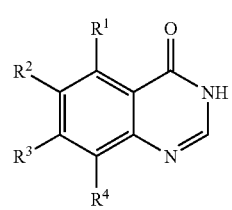

(1)

in which $R^1$, $R^2$, $R^3$ and $R^4$ have the same meaning as above, with a chlorinating agent in an amount of 1.0 to 2.5 moles based on one mole of the quinazolin-4-one compound, said chlorinating agent being selected from the group consisting of phosphorus oxychloride, phosphorus trichloride, phosphorus pentachloride, thionyl chloride, sulfuryl chloride and nitrosyl chloride, in a first organic solvent in the presence of an organic base, to give a reaction mixture containing a reaction product, and a second step comprising adding an amine compound having the formula (2) to the reaction mixture:

(2)

in which $R^5$ and $R^6$ have the same meaning as above, in the presence of a second organic solvent, wherein the first reaction solvent is selected from the group consisting of an aliphatic hydrocarbon, a halogenated aliphatic hydrocarbon, an aromatic hydrocarbon, and a halogenated aromatic hydrocarbon and wherein the second reaction solvent comprises the first reaction solvent and nitrile or ketone added thereto.

2. The process of claim 1, wherein each of $R^1$, $R^4$ and $R^6$ is hydrogen, each of $R^2$ and $R^3$ is 2-methoxyethoxy, and $R^5$ is 3-ethynylphenyl.

3. The process of claim 1, wherein each of $R^1$, $R^4$ and $R^6$ is hydrogen, $R^2$ is methoxy, $R^3$ is 3-morpholinopropoxy, and $R^5$ is 3-chloro-4-fluorophenyl.

4. The process of claim 1, wherein the quinazolin-4-one compound of formula (1) is 6-halogenoquinazolin-4-one of the following formula (4), the amine compound of formula (2) is arylamine of the following formula (5), and the 4-arylaminoquinazoline compound of formula (3) is 6-halogeno-4-arylaminoquinazoline of the following formula (6):

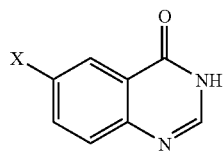

(4)

ArNH$_2$ (5)

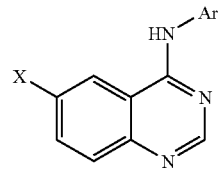

(6)

in which X is a halogen atom, and Ar is an aryl group which can have a substituent.

5. The process of claim 4, wherein X is iodine.

6. The process of claim 5, wherein Ar is 3-chloro-4-(3-fluorobenzyl-oxy)phenyl.

7. The process of claim 1, wherein the reaction of the first step is performed by adding the organic base to a mixture of the quinazolin-4-one compound, first organic solvent, and chlorinating agent.

8. The process of claim 1, wherein the organic base is used in an amount of 0.8 to 2.5 moles, based on one mole of the quinazolin-4-one compound.

9. The process of claim 1, wherein the first organic solvent is an aromatic hydrocarbon.

10. The process of claim 1, wherein the chlorinating agent is phosphorus oxychloride.

11. The process of claim 1, wherein each of the reactions of the first and second steps is performed at a temperature of 10 to 150° C.

* * * * *